United States Patent [19]

Cho et al.

[11] Patent Number: 5,534,649
[45] Date of Patent: Jul. 9, 1996

[54] PROCESS FOR PREPARING DIALKYL CARBONATES

[75] Inventors: Tsurahide Cho, Tokyo; Takaaki Tamura, Kawasaki; Toshitsura Cho, Tokyo; Kazumi Suzuki, Kawasaki, all of Japan

[73] Assignees: Tama Chemicals Co., Ltd., Tokyo, Japan; Moses Lake Industries, Inc., Moses Lake, Wash.

[21] Appl. No.: 365,846

[22] Filed: Dec. 29, 1994

[30] Foreign Application Priority Data

Oct. 21, 1994 [JP] Japan ................................. 6-257175

[51] Int. Cl.⁶ .................................................. C07C 68/00
[52] U.S. Cl. ................................................... 558/277
[58] Field of Search ...................................... 558/277

[56] References Cited

U.S. PATENT DOCUMENTS

| | | | |
|---|---|---|---|
| 2,834,799 | 5/1958 | Sowa | 558/277 |
| 4,327,035 | 4/1982 | Heitz et al. | 558/277 |
| 4,331,610 | 5/1982 | Heitz et al. | 558/277 X |
| 4,436,668 | 3/1984 | Harder et al. | 558/277 X |

FOREIGN PATENT DOCUMENTS

| | | |
|---|---|---|
| 54-41820 | 4/1979 | Japan . |
| 59-3463 | 1/1984 | Japan . |
| 2212456 | 8/1990 | Japan . |
| 4270249 | 9/1992 | Japan . |

OTHER PUBLICATIONS

English Language Abstract of Japanese Patent No. 4-270249 (A)(1992).

English Language Abstract of Japanese Patent No. 59-3463 (1984).

English Language Abstract of Japanese Patent No. 54-41820 (1979).

English Language Abstract of Japanese Patent No. 2-212456 (A)(1990).

*Primary Examiner*—Johann Richter
*Assistant Examiner*—Michael G. Ambrose
*Attorney, Agent, or Firm*—Birch, Stewart, Kolasch & Birch

[57] ABSTRACT

This invention relates to a process for preparing dialkyl carbonates by the reaction of one kind or a mixture of two or more kinds selected from urea, methyl carbamate and ethyl carbamate with methanol and/or ethanol in the presence of a catalyst under pressure at 100° to 250° C. and the process does not use poisonous phosgene or carbon monoxide as raw material and readily yields dimethyl carbonate and diethyl carbonate in simple equipment.

4 Claims, No Drawings

PROCESS FOR PREPARING DIALKYL CARBONATES

FIELD OF THE INVENTION AND RELATED ART STATEMENT

This invention relates to a process for preparing dialkyl carbonates in which the alkyl group is methyl or ethyl and, more particularly, to a process for preparing dialkyl carbonates starting with urea.

Processes known for the preparation of dimethyl carbonate and diethyl carbonate are based, for example, on the reaction of phosgene with methanol or ethanol or the reaction of carbon monoxide with methanol or ethanol in the presence of oxygen.

With the former process, however, poisonous phosgene is used as a raw material and it is troublesome to handle. Moreover, hydrogen chloride formed as byproduct corrodes the reactor and adjacent equipment and restricts reactors usable for the process.

On the other hand, the latter process with the use of carbon monoxide involves an oxidation reaction in the presence of oxygen and requires a manufacturing plant with precise control exercised over the composition of the reactants, the reaction pressure, the reaction temperature and the like. Although suitable for large-volume production, this process requires high equipment cost and is not adequate where small- or medium-volume production is intended with simple equipment.

OBJECT AND SUMMARY OF THE INVENTION

The present inventors have conducted extensive studies to develop a process for preparing dialkyl carbonates free from the aforementioned problems, found that the intended dimethyl carbonate or diethyl carbonate can be prepared by using urea or methyl carbamate or ethyl carbamate which is obtained by the reaction of urea with methanol or ethanol as raw material and allowing such raw material to react with methanol or ethanol in the presence of a specified catalyst and completed this invention.

It is accordingly an object of this invention to provide a novel process for preparing dialkyl carbonates without the use of poisonous phosgene or carbon monoxide as raw material readily in simple equipment.

This invention thus relates to a process for preparing dialkyl carbonates which comprises conducting the reaction of one kind or a mixture of two or more kinds selected from urea, methyl carbamate and ethyl carbamate with methanol and/or ethanol in the presence of a catalyst under pressure at 100° to 250 ° C.

Urea, methyl carbamate and ethyl carbamate as raw material in this invention may be used singly or as a mixture of two or more. Methyl carbamate and ethyl carbamate can be prepared readily by the reaction of urea with methanol and ethanol and they constitute intermediates of the process of this invention when urea is used as raw material.

Catalysts useful for this invention are alkali metal compounds such as hydroxides, carbonates, methoxides, ethoxides and carbamates, quaternary ammonium compounds such as hydroxides, carbonates, hydrogencarbonates, hydrogencarbonate esters and carbamates of tetramethylammonium and tetraethylammonium and tertiary amines such as trimethylamine (TrMA) and triethylamine (TrEA), applied either singly or as a mixture of two or more.

Concrete examples of the alkali metal compounds are sodium hydroxide, potassium hydroxide, rubidium hydroxide (RbOH) and cesium hydroxide (CsOH) for alkali metal hydroxides; sodium carbonate, potassium carbonate, rubidium carbonate ($Rb_2CO_3$) and cesium carbonate ($Cs_2CO_3$) for alkali metal carbonates; sodium methoxide ($CH_3ONa$), sodium ethoxide ($C_2H_5ONa$), potassium methoxide ($CH_3OK$) and potassium ethoxide ($C_2H_5OK$) for alkali metal methoxides and ethoxides; and sodium carbamate and potassium carbamate for alkali metal carbamates. Examples of quaternary tetramethylammonium or tetraethylammonium compounds are tetramethylammonium hydroxide (TMAH) and tetraethylammonium hydroxide (TEAH) for hydroxides; ditetramethylammonium carbonate and ditetraethylammonium carbonate for carbonates; tetramethylammonium hydrogencarbonate and tetraethylammonium hydrogencarbonate for hydrogencarbonates; tetramethylammonium hydrogencarbonate methyl ester and tetraethylammonium hydrogencarbonate ethyl ester for hydrogencarbonate esters; and tetramethylammonium carbamate and tetraethylammonium carbamate for carbamates.

In case an alkali metal methoxide or ethoxide as alkali metal compound, a quaternary ammonium compound, or a tertiary amine is used as catalyst, it is desirable for the alkyl group in the catalyst to be identical with that in the target product. Where dimethyl carbonate is the target, for example, it is preferable to use alkali metal methoxide, tetramethylammonium compound, or trimethylamine (TMA).

The amount of methyl alcohol or ethyl alcohol in relation to urea or methyl carbamate or ethyl carbamate is normally 0.5 top 10 mol equivalent, preferably 2 to 5 mol equivalent. The amount of the catalyst is normally 0.005 to 0.2 mol equivalent, preferably 0.03 to 0.06 mol equivalent.

It is preferable to carry out the reaction of urea or methyl carbamate or ethyl carbamate with methyl alcohol or ethyl alcohol at a temperature of 100° to 250° C., preferably at 130° to 160° C. and a pressure of 3 to 90 atmospheres, preferably 5 to 20 atmospheres.

It is desirable in this invention to remove from the reaction system ammonia gas formed as byproduct in the reaction of urea, methyl carbamate or ethyl carbamate with methyl alcohol or ethyl alcohol. The merit of this procedure is supported by the results in Examples 11 and 15. The process for the removal of byproduct ammonia gas is not specified and the removal can be effected by attaching a fractionation column to the reactor and separate ammonia from other high-boiling components or adding to the reaction system deammoniation agents which react with ammonia and remove it, such as hydrogenated molecular sieves.

The product dialkyl carbonates formed in the reaction in this invention are separated from the reaction mixture by fractionation under pressure as disclosed, for example, in Japan Tokkyo Koho No. Sho 59-3,463 (1984) and Japan Kokai Tokkyo Koho No. Hei 2-212,456 (1990), by fractionation under normal pressure as disclosed in Japan Kokai Tokkyo Koho No. Sho 54-41,820 (1979), or by extractive distillation in the presence of an azeotrope-forming agent as disclosed in Japan Kokai Tokkyo Koho No. Hei 4-270,249 (1992) and purified. The process of this invention makes it possible to prepare dimethyl carbonate and diethyl carbonate without the use of poisonous phosgene or carbon monoxide as raw material readily in simple equipment and it is suitable for small-volume and medium-volume production of dialkyl carbonates as the equipment cost does not run up.

DETAILED DESCRIPTION OF THE PREFERRED EMBODIMENTS

This invention will be described in detail below with reference to the accompanying examples and comparative example.

Examples 1 to 9 and Comparative Example 1

Into a sealed reactor were introduced 3 moles of methyl carbamate, 17 moles of methanol and 0.5 mole of the catalyst shown in Table 1 and the mixture was allowed to react at 160° C. and 20 atmospheres for 5 hours.

Upon completion of the reaction, the reaction mixture was distilled at normal pressure, the distillate was analyzed by gas chromatography and the yield of the product dimethyl carbonate based on the raw material methyl carbamate was determined. The results are shown in Table 1.

TABLE 1

| Catalyst | Yield (%) | | Catalyst | Yield (%) |
|---|---|---|---|---|
| Comparative example 1 | — | <0.05 | Example 5 | $CH_3ONa$ | 0.96 |
| Example 1 | CsOH | 0.24 | Example 6 | TMAH | 1.10 |
| Example 2 | $Cs_2CO_3$ | 1.85 | | | |
| Example 3 | $K_2CO_3$ | 0.44 | Example 7 | MMCTMA | 4.13 |
| Example 4 | $Na_2CO_3$ | 1.53 | | | |
| | | | Example 8 | CATMA | 4.07 |
| | | | Example 9 | TrMA | 2.20 |

TMAH: Tetramethylammonium hydroxide
MMCTMA: Tetramethylammonium hydrogencarbonate methyl ester
CATMA: Tetramethylammonium carbamate
TrMA: Trimethylamine

Example 10 and Comparative Example 2

The reaction was carried out as in the aforementioned examples by replacing methyl carbamate with urea and using tetraethylammonium hydrogencarbonate methyl ester (MMCTMA) as catalyst in Example 10 or no catalyst in Comparative Example 2 and the yield of dimethyl carbonate based on the urea was determined.

The yield was 0.10% or less in Comparative Example 2 and 1.27% in Example 10.

Example 11

The reaction was carried out as in the aforementioned Example 1 except using tetramethylammonium hydrogencarbonate methyl ester (MMCTMA) and setting the reaction temperature at 145° C. and the yield of dimethyl carbonate was determined at intervals in the course of the reaction.

The yield was 1.99% after 9 hours, 4.41% after 18 hours, 6.03% after 36 hours and 5.91% after 74 hours.

Example 12

Into an autoclave were introduced 25.07 g (0.2814 mole) of ethyl carbamate, 55.77 g (1.2105 moles) of ethanol and 16.35 g (0.0502 mole) of $Cs_2CO_3$, the mixture was allowed to react at 150° C. and the maximum pressure of 18 kg/cm$^2$ for 5 hours and the yield of the product diethyl carbonate based on the ethyl carbamate was determined. The yield was 1.00%.

Example 13

Into an autoclave were introduced 25.07 g (0.2814 mole) of ethyl carbamate, 55.77 g (1.2101 moles) of ethanol and 5.38 g (0.0508 mole) of $Na_2CO_3$, the mixture was allowed to react at 160° C. and the maximum pressure of 15 kg/cm$^2$ for 5 hours and the yield of the product diethyl carbonate based on the ethyl carbamate was determined. The yield was 1.03%.

Example 14

Urea was subjected to the reaction as in Example 10 in a reactor equipped in its upper portion with a fractional distillation column having a theoretical plate number of 15 under the conditions where the temperature of the cooler at the top of the distillation column was kept at 25° C. and the pressure inside the column was kept at 9.5 atmospheres gauge and the byproduct ammonia gas was withdrawn from the column top.

The yield of dimethyl carbonate determined at intervals in the course of the reaction was 7.5% after 26 hours, 15.2% after 53 hours and 18.3% after 74 hours.

Example 15

Methyl carbamate was subjected to the reaction as in Example 11 in the same reactor as used in Example 14 and the yield of dimethyl carbonate was determined at intervals in the course of the reaction.

The yield was 11.8% after 30 hours, 16.1% after 54 hours, 20.2% after 83 hours and 18.5% after 104 hours.

What is claimed is:

1. A process for preparing dialkyl carbonates comprising the step of reacting one or a mixture of two or more compounds selected from the group consisting of urea, methyl carbamate and ethyl carbamate, with methanol and/or ethanol in the presence of a quaternary ammonium compound catalyst under pressure at a temperature of 100° to 250° C.

2. The process according to claim 1, wherein the catalyst is tetramethylammonium carbonate, tetraethylammonium carbonate, tetramethylammonium hydrogencarbonate, tetraethylammonium hydrogencarbonate, tetramethylammonium hydrogencarbonate methyl ester, tetraethylammonium hydrogencarbonate ethyl ester, tetramethylammonium carbamate or tetraethylammonium carbamate.

3. The process according to claim 1, where ammonia gas formed in the reaction is removed from the reaction system.

4. The process according to claim 2, where ammonia gas formed in the reaction is removed from the reaction system.

* * * * *